US006579228B2

(12) United States Patent
Lien

(10) Patent No.: US 6,579,228 B2
(45) Date of Patent: Jun. 17, 2003

(54) THERAPEUTIC AID APPARATUS AND METHOD

(76) Inventor: Gary W. Lien, 4309 E. Valley Hwy., Sumner, WA (US) 98390

( * ) Notice: Subject to any disclaimer, the term of this patent is extended or adjusted under 35 U.S.C. 154(b) by 0 days.

(21) Appl. No.: 09/905,581

(22) Filed: Jul. 13, 2001

(65) Prior Publication Data

US 2002/0099261 A1 Jul. 25, 2002

Related U.S. Application Data

(60) Provisional application No. 60/218,227, filed on Jul. 14, 2000.

(51) Int. Cl.[7] .................................................. A61F 5/00
(52) U.S. Cl. ........................................................ 600/38
(58) Field of Search .......................... 600/38–41; 446/3, 446/429, 438, 430, 489

(56) References Cited

U.S. PATENT DOCUMENTS 3,504,665 A 4/1970 Bakunin et al.
3,626,931 A 12/1971 Bysakh
3,726,273 A 4/1973 Cole
3,744,767 A * 7/1973 Blasnik ...................... 366/243
3,910,262 A 10/1975 Stoughton
3,991,751 A 11/1976 O'Rourke
4,050,449 A 9/1977 Castellana et al.
4,149,530 A 4/1979 Gow
4,574,791 A 3/1986 Mitchener
4,722,327 A 2/1988 Harvey
4,790,296 A 12/1988 Segal
4,846,158 A 7/1989 Teranishi
4,989,592 A 2/1991 Chang
5,067,480 A 11/1991 Woog et al.
5,127,396 A 7/1992 McAllister
5,178,920 A * 1/1993 Stone ......................... 280/727
5,460,597 A 10/1995 Hopper
5,470,303 A 11/1995 Leonard et al.
5,725,473 A 3/1998 Taylor
5,782,745 A 7/1998 Benderev
5,853,362 A 12/1998 Jacobs
6,364,719 B1 * 4/2002 Chopra ....................... 439/759
6,399,865 B1 * 6/2002 Ishimatsu .................... 84/421

* cited by examiner

*Primary Examiner*—Samuel G. Gilbert

(57) ABSTRACT

A therapeutic aid includes an elongate centrally disposed shaft with a head coupled to one end thereof for removably receiving a phallus device. To support the shaft in a first extended position, a biasing element is disposed adjacent the shaft. A retaining member is disposed adjacent the head for retaining a portion of the biasing element in relation to the shaft. A slide seat is slidingly received by the shaft, and is fixed to an opposing portion of the biasing element such that the shaft is movable from a first extended position where the head is disposed at its furthest point from the slide seat, to a second compressed position where the head is urged toward the slide seat as the slide seat slides along the shaft to compress the biasing element between the retaining member and the slide seat.

20 Claims, 5 Drawing Sheets

THERAPEUTIC AID APPARATUS AND METHOD

This application claims the benefit of U.S. Provisional Application No. 60/218,227 filed Jul. 14, 2000.

BACKGROUND

This invention relates generally to therapeutic aids provided to improve the sexual relationship between sexual partners, and more particularly to mechanical aids that enable a partner alternate means for female stimulation.

Therapeutic aids and mechanisms provided to improve the sexual relationship between sexual partners are known in the art. Such aids vary widely in complexity, ease of operation and cost of manufacturing and maintaining. Many such devices require hand operation and/or activation by an electrical source. For example, in 1970, U.S. Pat. No. 3,504,665 issued disclosing an electrically activated medical gynecologic oscillator for stimulating the clitoral areas of a woman. The device is complex in design, and requires many moving parts. In 1971 U.S. Pat. No. 3,626,931 issued disclosing an electrically operated vibrator device for vibrating the erotic parts of the female genitalia. In 1975 U.S. Pat. No. 3,910,262 issued disclosing an electrically operated therapeutic apparatus comprising a motor driven piston for producing orgasms. In 1976 U.S. Pat. No. 3,991,751 issued disclosing an electrically operated hand-held stimulation device.

Alternately, non-electrically operated devices include U.S. Pat. No. 3,726,273 issued in 1973 disclosing a muscle exercising device for exercising the muscles of the vagina wherein the device employed a plurality of separated bulbs. This invention required hand activation. Similarly, in 1977 U.S. Pat. No. 4,050,449 issued disclosing a balloon apparatus for actuation by air or the like for exercising muscles of a female pelvic diaphragm. Further, U.S. Pat. No. 4,574,791 issued in 1986 disclosing a muscle-toning device for the female pelvic structure comprising a vaginal insert connected to a flexible cable to an exteriorly disposed support body activated by the user's hand. Also, in 1988, U.S. Pat. No. 4,722,327 disclosed a rail mounted platform disposed for reciprocal motion along the tracks wherein the platform included an artificial penis.

Other electrically operated devices include U.S. Pat. No. 4,149,530 disclosing a hand held portable electric vibrator for electrically massaging the user; U.S. Pat. No. 4,790,296 disclosed an electrically operated apparatus for engaging the glans of a user for sexual stimulation. Moreover, U.S. Pat. Nos. 4,846,158, 5,067,480, 5,460,597 and 5,470,303 disclose other similar hand operated electric vibrating devices.

Examples of other electric motor operated devices include U.S. Pat. Nos. 5,725,473 disclosing a motor operated sexual aid having a housing mounted on a detachable legs, and 5,782,745 showing a motor operated device adapted to be inserted with an anatomical passageway to provide periodic stimulus to wall or muscles by way of pressure, stretching, vibration, or heat.

Finally, various other stimulation devices include U.S. Pat. No. 4,989,592 disclosing a user worn waist band incorporating a flexible glans penis shaped structure. U.S. Pat. No. 5,127,396 disclosing a system including a phallus device mounted on a plug formed a rigid material, and U.S. Pat. No. 5,853,362 disclosing a hook shaped glandular stimulator device shaped to be worn internally by a woman. Each of these required the user to employ his or her hands in the operation thereof.

As can be seen from the above noted prior art, devices directed to aiding sexual stimulus typically are electrically activated and/or require the user to hand operate the same. In addition, they are some what complex in structure and may require tedious cleaning procedures. Accordingly, a need remains for a simple device to improve sexual relations between partners that is adaptable for activation with or without the use of hands, and with or without the use of electric motors.

SUMMARY

One object of the invention is to allow a disabled individual to easily stimulate a sexual partner.

A second object is to enable a person alternate means to stimulate a sexual partner.

Another object is to improve sexual relations between partners.

Yet another object is eliminate the need for electrically operated stimulation devices.

A further object is simplify mechanically operated stimulation devices.

Still another object is to enable the option to eliminate the need for hand operating a device in the stimulation activity of sexual partners where one partner is disabled.

The invention is a therapeutic aid provided to enhance and improve the sexual relationship between partners. For that purpose, the therapeutic aid is adapted to receive a phallus or other similarly shaped device. Specifically, the therapeutic aid comprises an elongate centrally disposed shaft with a head coupled to one end thereof for removably receiving the phallus device.

In order to support the shaft in a first extended position, a biasing element is disposed adjacent the shaft. Further, a retaining member is disposed adjacent the head for retaining a portion of the biasing element in relation to the shaft. Importantly, a slide seat is slidingly received by the shaft, and is fixed to an opposing portion of the biasing element such that the shaft is movable from a first extended position where the head is disposed at its furthest point from the slide seat, to a second compressed position where the head is urged toward the slide seat as the slide seat slides along the shaft to compress the biasing element between the retaining member and the slide seat. With this arrangement, a user can manipulate the therapeutic aid by grasping the slide member to apply a varying pressure, the pressure being directed substantially coaxially with the shaft, to the phallus device which is provided for placement within a woman's vagina.

In another aspect of the invention, the therapeutic aid further comprises an elongate vertically oriented pedestal assembly. The pedestal assembly includes a lower end configured for attachment to a base which is provided for placement on a substantially flat horizontal surface/floor. In addition, the pedestal assembly includes an opposing upper end adapted to supportively engage the slide seat for retaining a portion of the biasing element in relation to the pedestal assembly.

The foregoing and other objects, features, and advantages of this invention will become more readily apparent from the following detailed description of a preferred embodiment which proceeds with reference to the accompanying drawings, wherein the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION OF PREFERRED EMBODIMENT

Figure 1:
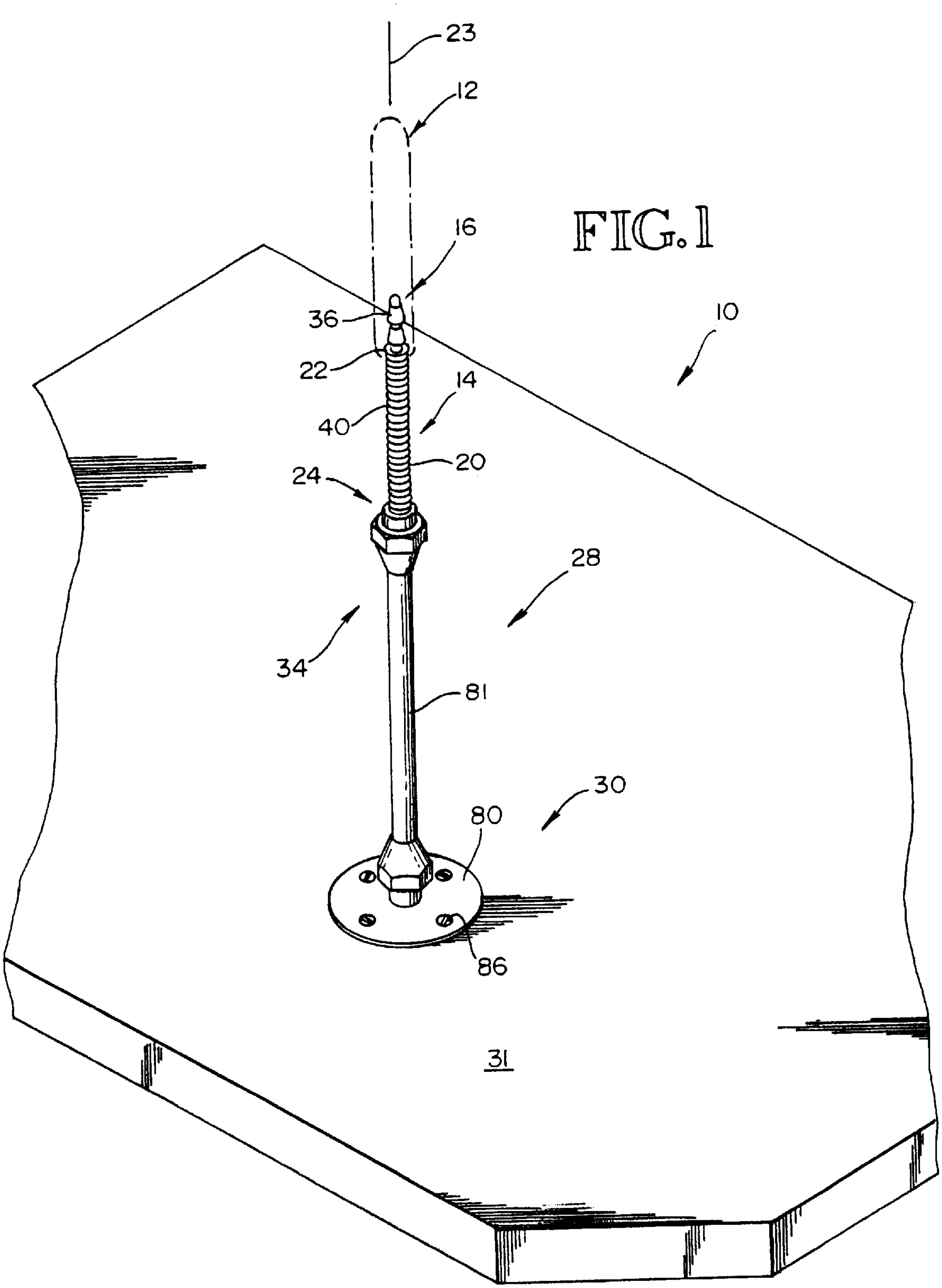
FIG. 1 is a perspective view of the preferred embodiment of a therapeutic aid.
Figure 2:
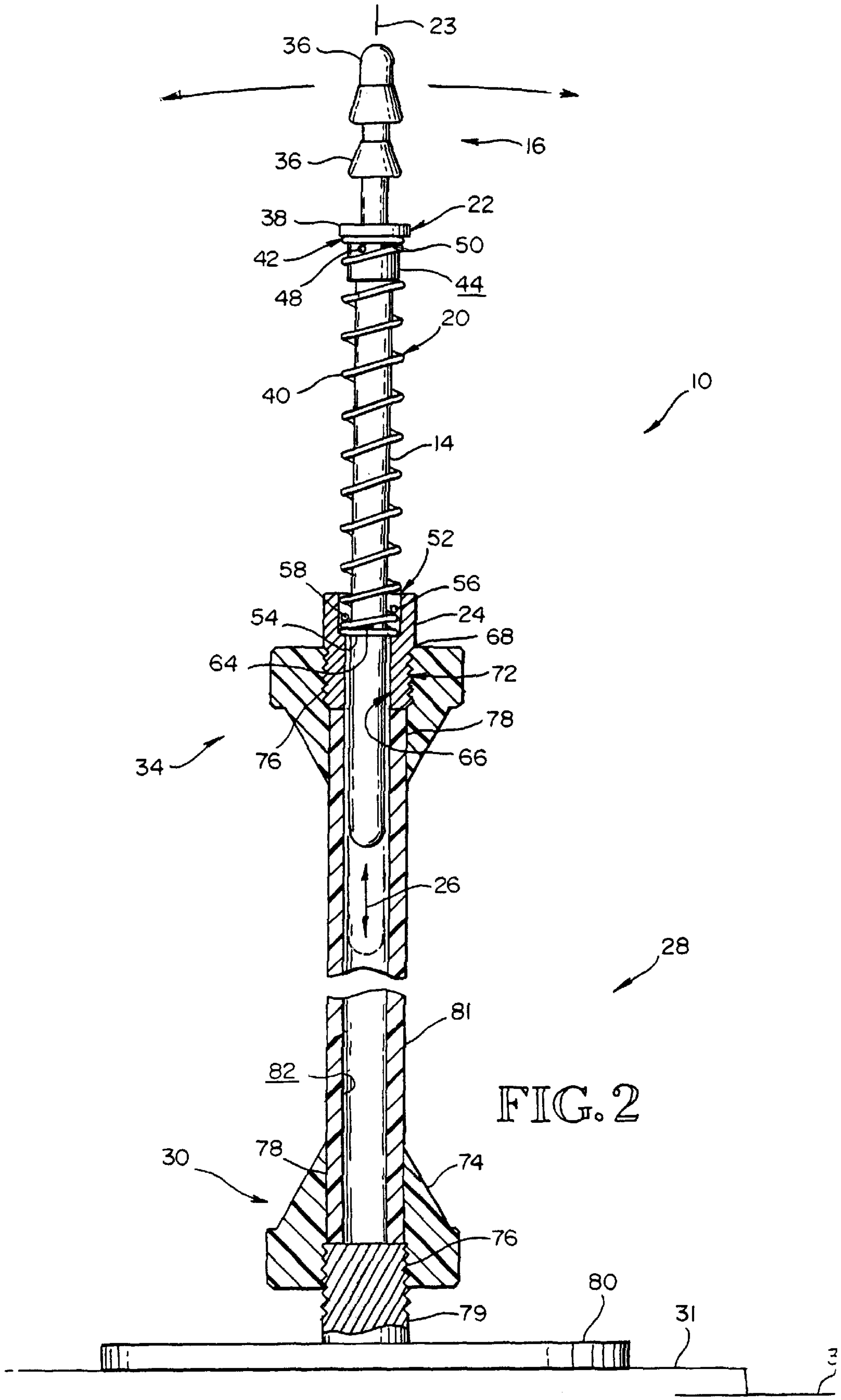
FIG. 2 is an elevational view of a therapeutic aid with portions broken away to illustrate the slide seat attachment to the pedestal assembly.
Figure 3:
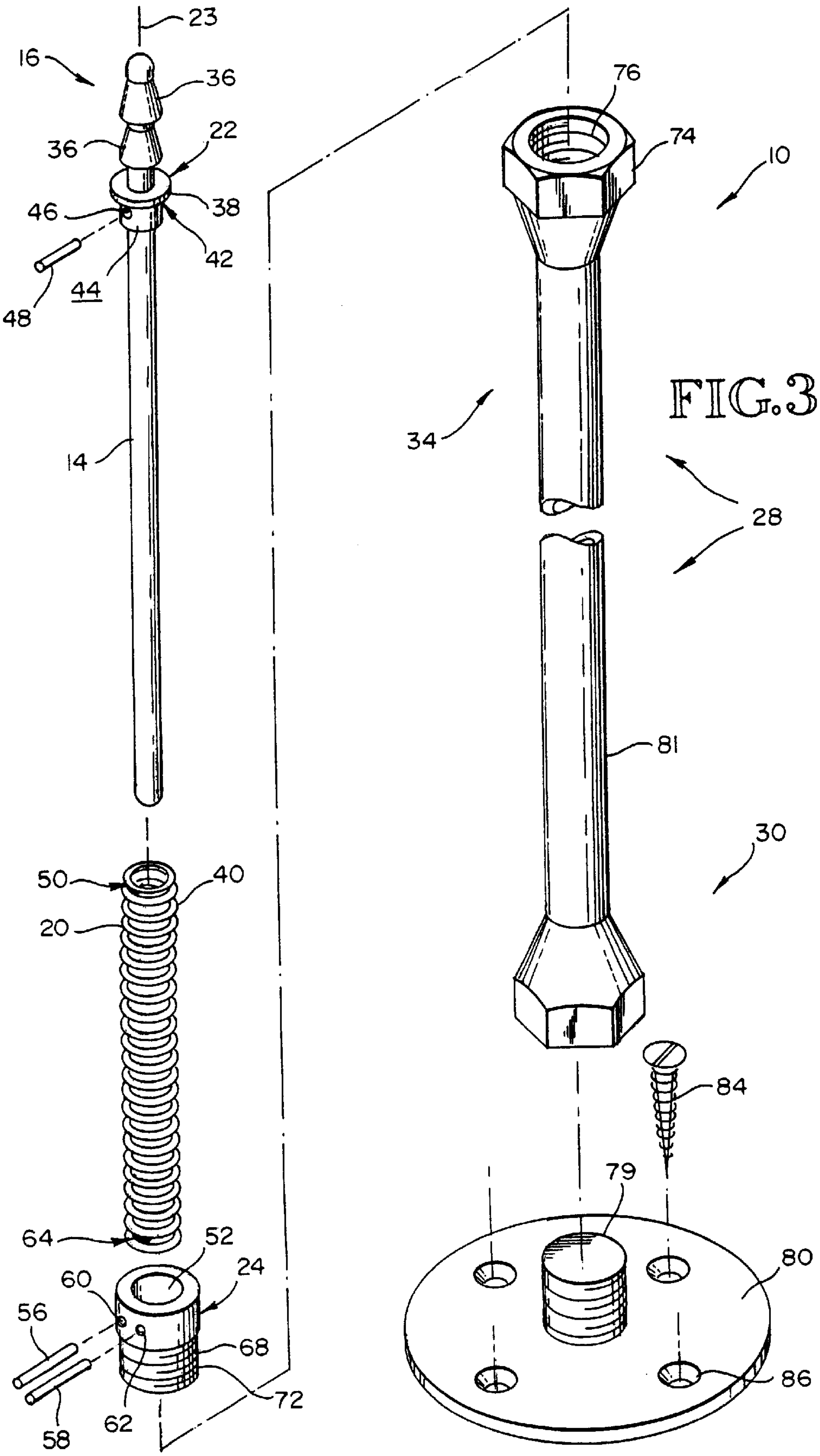
FIG. 3 is an exploded perspective view illustrating the components of a therapeutic aid.

FIGS. 1 through 3 illustrate a preferred embodiment of the present invention. Indicated generally at 10 is a therapeutic aid 10 provided to enhance and improve the sexual relationship between partners. For that purpose, the therapeutic aid 10 is adapted to receive a phallus device 12 or other similarly shaped device. Specifically, the therapeutic aid 10 comprises an elongate centrally disposed shaft 14 with a head 16 coupled to one end thereof for removably receiving the phallus device 12. In order to support the shaft 14 in a first extended position (FIGS. 1 and 2), a biasing element 20 is disposed adjacent the shaft 14.

Further, a retaining member 22 is disposed adjacent the head 16 for retaining a portion of the biasing element 20 in relation to the shaft 14. Importantly, a slide seat 24 is slidingly received by the shaft 14, and is fixed to an opposing portion of the biasing element 20 such that the shaft 14 is movable from a first extended position where the head 16 is disposed at its furthest point from the slide seat 24 (FIGS. 1 and 2), to a second compressed position (not illustrated) where the head 16 is urged toward the slide seat 24 as the slide seat 24 slides along the shaft 14 to compress the biasing element 20 between the retaining member 22 and the slide seat 24. With this arrangement, a user can manipulate the therapeutic aid 10 by grasping the slide member 22 to apply a varying pressure to the phallus device 12. It should be noted that the cyclical motion between the first extended position to the second compressed position is indicated by arrow 26.

In another aspect of the invention, the therapeutic aid 10 further comprises an elongate vertically oriented pedestal assembly 28 having a lower end 30 configured for attachment to a base 31 which is provided for placement on a substantially flat horizontal surface/floor 32. In addition, the pedestal assembly 28 includes an opposing upper end 34 adapted to supportively engage the slide seat 24 for retaining a portion of the biasing element 20 in relation to the pedestal assembly 28.

Considering now in more detail the structure of the components from which a therapeutic aid 10 is constructed, generally the preferred embodiment includes a shaft 14, head 16, and a retaining member 22 integrally fabricated, e.g., turned on a lath, from a solid piece of aluminum about an axis 23. Although this construction is employed, other materials, including plastic could easily be substituted with equally satisfactory results.

Importantly, in the preferred embodiment, the head 16 is formed at one end of the shaft 14, and includes at least one barb 36, wherein the preferred embodiment includes two spaced-apart alike barbs 36. Each barb 36 is symmetrically formed about the axis 23, and is provided to facilitate a secure attachment of a phallus device 12.

Similarly, a retaining member 22 is integrally formed with the shaft 14 and is disposed to receive a biasing element 20. As will be explained more fully below, the biasing element 20 is a spring 40 which is disposed about the shaft 14. For this purpose, the retaining member 22 is formed to define a flange 38 located adjacent the barbs 36. Accordingly a shoulder 42 is defined by one side of the flange 38 which therein creates a surface upon which the biasing element 20/spring 40 rests and is compressed against as noted below.

Additionally, the retaining member 22 includes a radially outer surface 44 disposed adjacent the shoulder 42, and is sized, in diameter, so that the spring 40 snugly extends thereover. In this way, a bore 46 can be provided through the retaining member 22 so that a pin 48, sized for an interference fit therein, can be employed to extend slightly beyond the radially outer surface 44. A pin 48 so disposed secures the spring 40 to the retaining member 22 as illustrated in FIGS. 2–3. As an additional measure, a weld 50, is provided at the end of the spring 40, at the point where the spring terminates upon itself. This creates a more secure attachment to the pin 48, and therefore to the retaining member 22 by impeding the spring 40 from pulling away from the pin 48. It should be noted that, although the retaining member 22 is integrally formed with the shaft 14, in the preferred embodiment, it could just as well be manufactured as a separate component that would fit over the shaft 14.

At the other end of the spring 40, a slide seat 24 is attached thereto. A slide seat 24 is provided as a component for compressing the spring 40 which in turn urges the head 16 in the direction of the axis 23. For this purpose, the slide seat 24 is constructed from a solid piece of material, aluminum in the preferred embodiment, to define a counter bore 52 sized to receive the spring 40.

Accordingly, a shoulder 54 is created at the bottom of the counter bore 52 which provides a surface for the spring 40 to press against wherein pressure can be applied to the spring 40 to compress the same. In order to fix the spring 40 to the slide seat 24, a pair of alike pins 56–58 are provided for an interference fit into bores 60–62, similar to pin 48 as noted above. Similarly, a weld 64 is provided to weld the spring 40 to itself for a secure connection to the slide seat 24 via pins 56, 58. As best illustrated in FIG. 3, the pins 56, 58 extend through the slide seat 24, through the counter bore 52 and spring 40 thereby creating a secure attachment between the spring 40 and the slide seat 24.

Directing attention to FIGS. 2, it should be noted that the slide seat 24 is constructed to define a shaft bore 66 which extends from the shoulder 54 of counter bore 53 entirely through the slide seat 24 and is sized to slidingly receive the shaft 14 therethrough. In this way, the slide seat 24 can slide up and down the shaft 14 to compress and uncompress the spring 40. As noted above, the slide seat 24 is slidingly received by the shaft 14, and is fixed to spring 40 such that the shaft 14 is movable from a first extended position where the head 16 is disposed at its furthest point from the slide seat 24 (FIGS. 1 and 2), to a second compressed position (not illustrated) where the head 16 is urged toward the slide seat 24 as the slide seat 24 slides along the shaft 14 to compress the biasing element 20 between the retaining member 22 and the slide seat 24.

Further, the slide seat 24 is constructed to define a radially outer surface 68 which can be employed for connection to a pedestal assembly 28, as noted below, or employed as a surface for grasping by a persons hand (not illustrated). To this end the radially outer surface 68 is formed to define threads 72 which enable threaded attachment to a portion of a pedestal assembly 28 as noted below.

Specifically, a pedestal assembly 28 includes an upper end 34 that comprises a threaded coupler 74 configured to threadedly engage the slide seat 24 as illustrated in FIGS. 2 and 3. In the preferred embodiment, the coupler 74 is a common pipe fitting that has a threaded bore 76, and an opposing smooth bore 78 for fitting over tubular member, i.e., a smooth pipe 81. This construction provides a convenient structure including a radially inner surface 82 within which the shaft 14 can travel in a cyclical back and forth motion as the same is moves from the first extended position to the second compressed position. Moreover, the pedestal assembly 28 includes an opposing lower end 30 having an identical coupler 74 which threadedly engages the threaded post 79 of a mounting flange 80. In this way, the mounting flange 80 can be secured to a base 31 by one or more screws that are disposed through fastener bores 86. With this construction, the base 31 can be placed upon a flat horizontal surface 32 so that the therapeutic aid 10 stands vertically upward. Importantly, in the preferred embodiment, each coupler 74, and the pipe 81 that extends therebetween, is constructed from readily available flexible plastic materials such as PVC. This type of construction produces a pedestal that can be easily manipulated from side to side for ease of use by the user.

Further, it should be understood that the biasing element 20 could be constructed and implemented in other ways. For example, the spring 40 of the preferred embodiment could be replaced with a tubular flexible material (not illustrated) that would fit over the shaft 14 in the same manner as spring 40.

Figure 4:
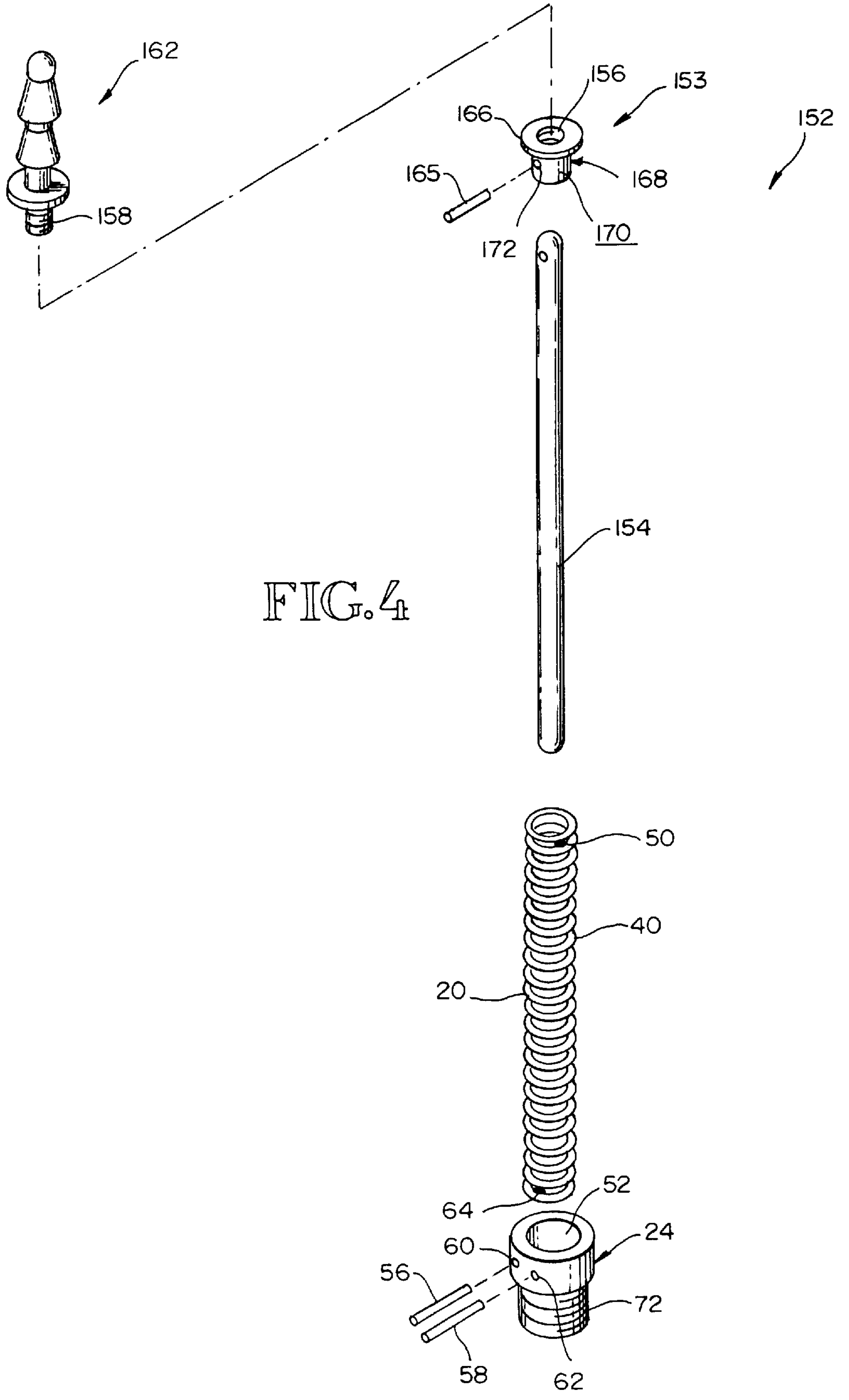
FIG. 4 is an exploded perspective view illustrating the components of an alternate embodiment having a detachable retaining member that includes a threaded bore provided to threadedly receive and engage various head attachments having a threaded post.
Figure 5:
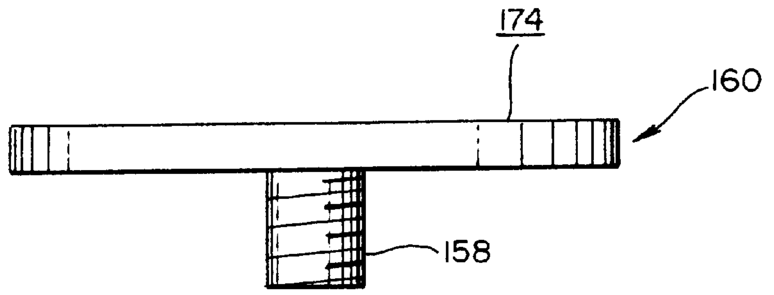
FIG. 5 is an elevational view illustrating a detachable surface head having a flat surface wherein the surface head includes a threaded post for threaded engagement and attachment to the threaded bore of the detachable retaining member.
Figure 6:
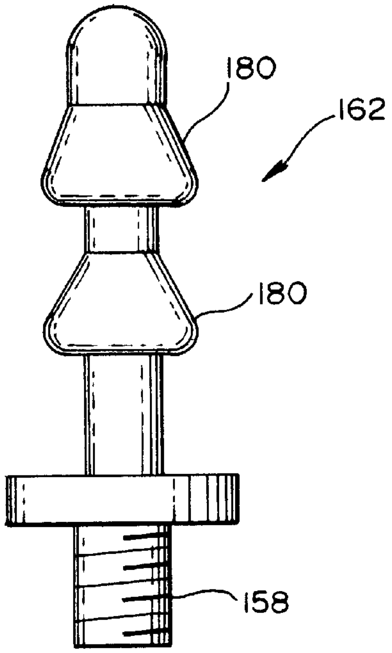
FIG. 6 is an elevational view illustrating a detachable barbed head configured to receive a phallus device wherein the barbed head includes a threaded post for threaded engagement and attachment to the threaded bore of the detachable retaining member.
Figure 7:
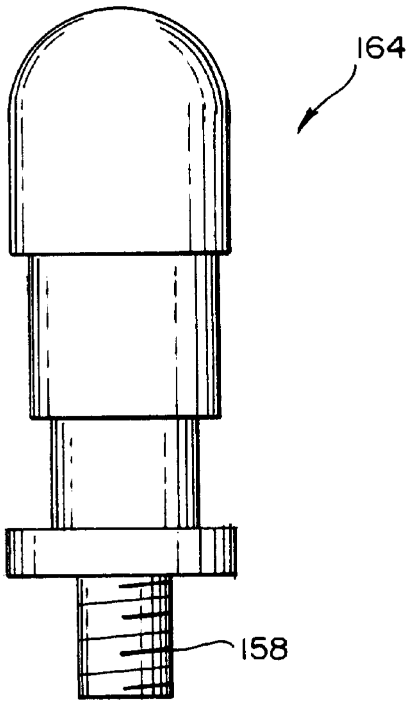
FIG. 7 is an elevational view illustrating a modified detachable barb shaped head that includes a threaded post for threaded engagement and attachment to the threaded bore of the detachable retaining member.

In another aspect of the invention, an alternate embodiment therapeutic aid 152 is illustrated in FIGS. 4 through 7. Specifically, this embodiment is directed to a detachable retaining member 153 which can be easily removed from a shaft 154. Importantly, the detachable retaining member 153 is formed to define a threaded bore 156 that is provided for threaded engagement with various head attachments. For this purpose, the various head attachments are formed to define a uniform threaded post 158 which is substantially identical on each head attachment. To this end, FIGS. 5, 6 and 7 illustrate three different types of head attachments including a detachable surface head 160 in FIG. 5; a detachable barbed head 162 in FIG. 6; and a modified detachable barb shaped head 164 in FIG. 7.

Importantly, the alternate embodiment therapeutic aid 152 incorporates substantially the same construction as the preferred embodiment except for the detachable retaining member 153 and the detachable heads 160, 162 and 164 that threadedly engage the same. Accordingly, the detachable retaining member 153 is removable mounted to the shaft 154 by a pin 165 which is disposed through both the shaft 154 and the detachable retaining member 153. In addition, the pin 165 serves to retain the spring 40 as described earlier in the description of the preferred embodiment.

Like the preferred embodiment, the detachable retaining member 153 is formed to define a flange 166. Accordingly a shoulder 168 is defined by one side of the flange 166 which therein creates a surface upon which the spring 40 rests and is compressed against as noted below.

Additionally, the detachable retaining member 153 includes a radially outer surface 170 disposed adjacent the shoulder 168, and is sized, in diameter, so that the spring 40 snugly extends thereover. In this way, a bore 172 can be provided through the detachable retaining member 153 so that a pin 165, sized for an interference fit therein, can be employed to extend slightly beyond the radially outer surface 170. A pin 165 so disposed secures the spring 40 to the detachable retaining member 153 as illustrated in FIG. 4 As in the preferred embodiment, a weld 50, is provided at the end of the spring 40, at the point where the spring terminates upon itself. This creates a more secure attachment to the pin 165, and therefore to the detachable retaining member 153 by impeding the spring 40 from pulling away from the pin 165.

Regarding the connection between the detachable retaining member 153 and the detachable heads therefor, a threaded bore 156 facilitates quick changes between the various heads that each serve a specific purpose. For example, FIG. 5 illustrates a detachable surface head 160 that provides a flat surface 174. In this way, the detachable surface head 160 can engage additional attachment (not illustrated) that are maintained thereon by way of a suction cup device (not illustrated). In addition, FIG. 6 illustrates a detachable barbed head 162 having two identical barbs 180. Like the preferred embodiment, the detachable barbed head 162 is so configured to receive a phallus device. Similarly, a modified detachable barbed head 164 is illustrated in FIG. 7 wherein the same can be employed by the user with or without the use of a phallus device. As can be seen, each of the detachable heads are shaped to define a shoulder so that as the threaded post 158 engages the threaded bore 156 of the detachable retaining member 153, they securely and tightly compress against each other thereby forming a distinct unit.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

What is claimed is:

1. A therapeutic aid configured to receive a phallus device for improving the sexual relationship between sexual partners, the therapeutic aid comprising:

an elongate centrally disposed shaft;

a retaining member disposed adjacent one end of the shaft, wherein the retaining member is fixed relative to the shaft;

a biasing element disposed adjacent the retaining member for biasing and supporting the shaft in a first extended position;

a head means coupled to the retaining member for removably receiving a phallus device; and a slide seat slidingly received by the shaft, wherein the slide seat is fixed to an opposing portion of the biasing element such that the shaft is movable from a first extended position where the head means is disposed at its furthest point from the slide seat, to a second compressed position where the head means is urged toward the slide seat as the slide seat slides along the shaft to compress the biasing element between the retaining member and the slide seat.

2. A therapeutic aid as recited in claim 1 wherein the biasing element is an elongate spring coaxially disposed about the shaft with one end of the spring being fixed to the retaining member and the opposing end of the spring being fixed to the slide seat.

3. A therapeutic aid as recited in claim 2 wherein the slide seat defines a shaft bore that is coaxially disposed about the shaft.

4. A therapeutic aid as recited in claim 1 further comprising an elongate vertically oriented pedestal assembly having a lower end adapted to rest on a substantially flat horizontal surface, and an opposing upper end adapted to supportively engage the slide seat for maintaining a portion of the biasing element in relation to the pedestal assembly.

5. A therapeutic aid as recited in claim 4 wherein the slide seat defines a radially outer surface that engages the pedestal assembly adjacent the upper end thereof.

6. A therapeutic aid as recited in claim 5 wherein the radially outer surface of the slide seat is threaded so that the same can threadedly engage the pedestal assembly adjacent the upper end thereof.

7. A therapeutic aid as recited in claim 6 wherein the upper end of the pedestal assembly comprises a coupler having a centrally disposed threaded bore coaxially disposed to threadedly engage the threaded radially outer surface of the slide seat, and wherein a portion of the coupler comprises a bore to fixedly receive a tubular member that extends from the coupler to the lower end of the pedestal assembly.

8. A therapeutic aid as recited in claim 6 wherein the pedestal assembly comprises a pipe having a radially inner surface through which the shaft extends when the shaft is urged to the second compressed position.

9. A therapeutic aid as recited in claim 1 wherein the retaining member is detachable from the shaft.

10. A therapeutic aid as recited in claim 1 wherein the head means is detachable from the retaining member.

11. A method of making therapeutic aid configured to receive a phallus device for improving the sexual relationship between sexual partners, the steps comprising:

providing an elongate centrally disposed shaft;

fixing a retaining member adjacent one end of the shaft;

employing a biasing element disposed adjacent the retaining member for biasing and supporting the shaft in a first extended position;

coupling a head means to the retaining member for removably receiving a phallus device; and installing a slide seat to be slidingly received by the shaft, wherein the slide seat is fixed to an opposing portion of the biasing element such that the shaft is movable from a first extended position where the head means is disposed at its furthest point from the slide seat, to a second compressed position where the head means is urged toward the slide seat as the slide seat slides along the shaft to compress the biasing element between the retaining member and the slide seat.

12. A method for making a therapeutic aid as recited in claim 11 further comprising the step of making the retaining member detachable from the shaft.

13. A method of making a therapeutic aid as recited in claim 11 further comprising the step of making the head means detachable from the retaining member.

14. A method of making a therapeutic aid as recited in claim 13 wherein the biasing element is an elongate spring coaxially disposed about the shaft with one end of the spring being fixed to the retaining member and the opposing end of the spring being fixed to the slide seat.

15. A method of making a therapeutic aid as recited in claim 11 wherein the biasing element is an elongate spring coaxially disposed about the shaft with one end of the spring being fixed to the retaining member and the opposing end of the spring being fixed to the slide seat.

16. A method of making a therapeutic aid as recited in claim 11 further comprising the step of providing an elongate vertically oriented pedestal assembly having a lower end adapted to rest on a substantially flat horizontal surface, and an opposing upper end adapted to supportively engage the slide seat for maintaining a portion of the biasing element in relation to the pedestal assembly.

17. A therapeutic aid configured to receive a phallus device for improving the sexual relationship between sexual partners, the therapeutic aid comprising:

an elongate centrally disposed shaft;

a retaining member disposed adjacent one end of the shaft, wherein the retaining member is detachable to the shaft;

a biasing element disposed adjacent the retaining member for biasing and supporting the shaft in a first extended position;

a head means coupled to the retaining member for removably receiving a phallus device; and a slide seat slidingly received by the shaft, wherein the slide seat is fixed to an opposing portion of the biasing element such that the shaft is movable from a first extended position where the head means is disposed at its furthest point from the slide seat, to a second compressed position where the head means is urged toward the slide seat as the slide seat slides along the shaft to compress the biasing element between the retaining member and the slide seat.

18. A therapeutic aid as recited in claim 17 wherein the biasing element is an elongate spring coaxially disposed about the shaft with one end of the spring being fixed to the retaining member and the opposing end of the spring being fixed to the slide seat.

19. A therapeutic aid as recited in claim 18 further comprising an elongate vertically oriented pedestal assembly having a lower end adapted to rest on a substantially flat horizontal surface, and an opposing upper end adapted to supportively engage the slide seat for maintaining a portion of the biasing element in relation to the pedestal assembly.

20. A therapeutic aid as recited in claim 17 further comprising an elongate vertically oriented pedestal assembly having a lower end adapted to rest on a substantially flat horizontal surface, and an opposing upper end adapted to supportively engage the slide seat for maintaining a portion of the biasing element in relation to the pedestal assembly.

* * * * *